US012066802B2

(12) United States Patent
Varikooty et al.

(10) Patent No.: US 12,066,802 B2
(45) Date of Patent: *Aug. 20, 2024

(54) SYSTEM AND METHOD FOR MONITORING STORAGE CONDITIONS IN PARTICULATE GOODS

(71) Applicant: Amber Agriculture, Inc., Urbana, IL (US)

(72) Inventors: Joseph Liu Varikooty, Edison, NJ (US); Lucas Nelson Stanley Delbert Frye, Havana, IL (US)

(73) Assignee: Amber Agriculture, Inc., Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/585,420

(22) Filed: Jan. 26, 2022

(65) Prior Publication Data
US 2022/0365502 A1 Nov. 17, 2022

Related U.S. Application Data

(63) Continuation of application No. 16/006,535, filed on Jun. 12, 2018, now Pat. No. 11,269,304.
(Continued)

(51) Int. Cl.
G05B 19/04 (2006.01)
A01F 25/16 (2006.01)
G01N 33/02 (2006.01)
G05B 19/042 (2006.01)
H04W 4/38 (2018.01)
(Continued)

(52) U.S. Cl.
CPC ............ *G05B 19/042* (2013.01); *A01F 25/16* (2013.01); *G01N 33/025* (2013.01); *H04W 4/38* (2018.02); *G05B 15/02* (2013.01); *G05B 2219/2614* (2013.01); *H04W 84/18* (2013.01)

(58) Field of Classification Search
CPC .... A01F 25/16; G01N 33/025; G05B 19/042; G05B 15/02; G05B 2219/2614; H04W 84/18
See application file for complete search history.

(56) References Cited

U.S. PATENT DOCUMENTS 8,045,168 B2 * 10/2011 Missotten .............. G01N 21/85
356/448
9,070,268 B2 6/2015 Monacos et al.
(Continued)

FOREIGN PATENT DOCUMENTS

CN 103412539 A * 11/2013

OTHER PUBLICATIONS

Shi et al., PE2E Machine Translation of CN-103412539-A 2013, CN Patent Office, 1-11 (Year: 2013).*

*Primary Examiner* — Elias Desta
(74) *Attorney, Agent, or Firm* — Alpine Patents LLC; Brian Van Osdol

(57) ABSTRACT

A system and method for managing of a particulate bulk good that includes a set of wireless sensor nodes, wherein each wireless sensor node comprises a set of environmental sensors configured to collect condition data of the particulate bulk good proximal to the wireless sensor node; an analysis engine that is configured to generate a particulate state analysis from the condition data; and a task manager that is configured to act on the particulate state analysis.

19 Claims, 11 Drawing Sheets

Related U.S. Application Data

(60) Provisional application No. 62/518,505, filed on Jun. 12, 2017.

(51) Int. Cl.
    *G05B 15/02*     (2006.01)
    *H04W 84/18*     (2009.01)

(56) References Cited

U.S. PATENT DOCUMENTS

| | | |
|---|---|---|
| 9,551,737 B2 | 1/2017 | Bloemendaal et al. |
| 9,628,876 B2 | 4/2017 | McCleland et al. |
| 9,756,785 B2 * | 9/2017 | Butts .................. A01D 41/1272 |
| 11,269,304 B2 * | 3/2022 | Varikooty ............... H04W 4/38 |
| 2007/0291724 A1 | 12/2007 | Twitchell |
| 2012/0015665 A1 | 1/2012 | Farley et al. |
| 2015/0177114 A1 | 6/2015 | Kapoor et al. |
| 2018/0197135 A1 | 7/2018 | Moyer et al. |
| 2019/0265082 A1 | 8/2019 | Zafar et al. |

* cited by examiner

SYSTEM AND METHOD FOR MONITORING STORAGE CONDITIONS IN PARTICULATE GOODS

CROSS-REFERENCE TO RELATED APPLICATIONS

This application is a Continuation Application of U.S. patent application Ser. No. 16/006,535, filed on 12 Jun. 2018, which claims the benefit of U.S. Provisional Application No. 62/518,505, filed on 12 Jun. 2017, both of which are incorporated in their entirety by this reference.

TECHNICAL FIELD

This invention relates generally to the field of material tracking, and more specifically to a new and useful system and method for monitoring storage conditions in particulate goods.

BACKGROUND

Agriculture has seen many advances that use modern sensing technology and data analysis to improve yields. As one particular use case, sensors in grain storage have been used to monitor the condition of the grain as it is stored. Many recent systems leverage sensor probes that are permanently installed in a grain bin. Such systems require significant investment in equipment, installation, and maintenance. As one problem, the harsh environmental conditions of these systems result in a short lifespan, and when the system encounters issues, an operator often will abandon use of the systems due to the cost and the complexity to make a repair. Furthermore, the permanent fixture of the sensor probes in a grain bin restricts any tracking of grain to only the grain bin. Thus, there is a need in the material tracking field and more specifically the agricultural supply-tracking field to create a new and useful system and method for managing particulate bulk good. This invention provides such.

DESCRIPTION OF THE EMBODIMENTS

Figure 1:
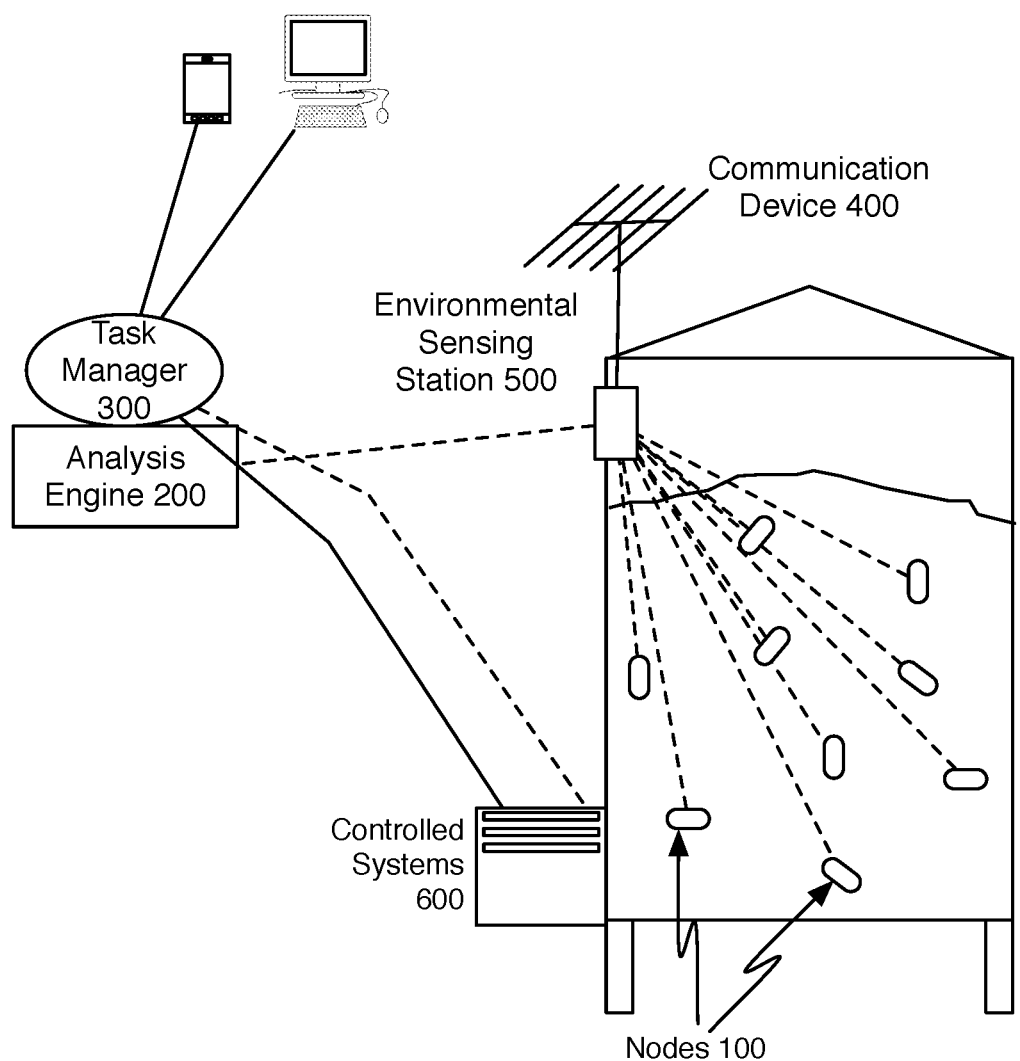
FIG. 1 is a schematic representation of a system of a preferred embodiment.
Figure 2:
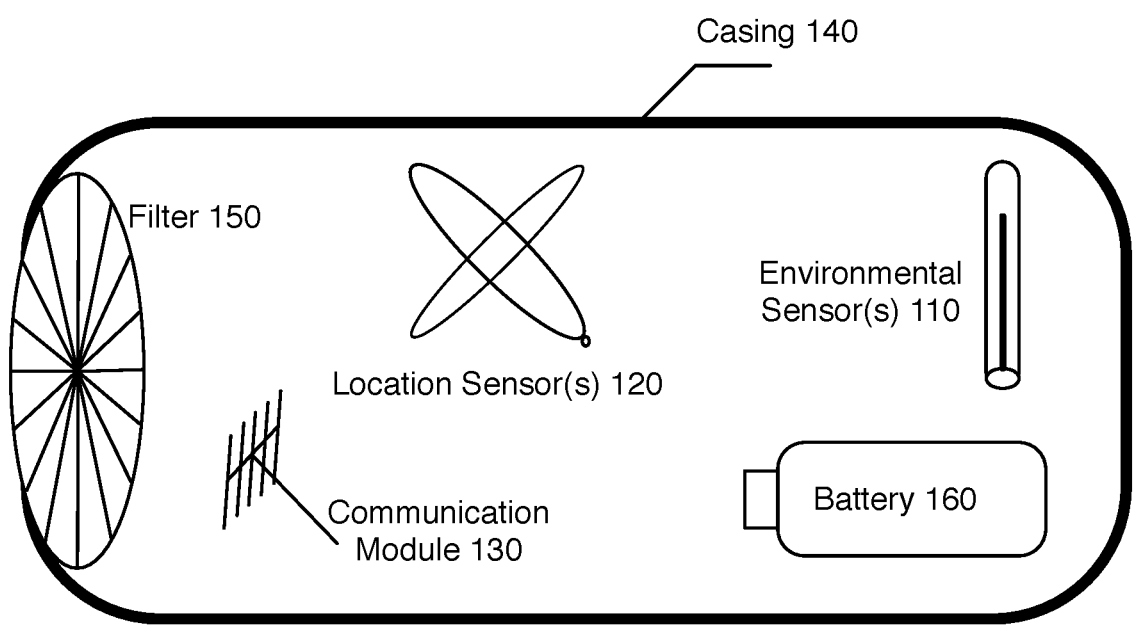
FIG. 2 is a generic schematic representation of a node, a subset of the goods monitoring and managing system.

The following description of the embodiments of the invention is not intended to limit the invention to these embodiments but rather to enable a person skilled in the art to make and use this invention.

1. Overview

A system and method for monitoring storage conditions of bulk goods of a preferred embodiment uses a set of wireless sensor nodes that can be distributed within a collection of particulate bulk goods and coordinates with an analysis engine and task manager. The system and method preferably function to augment the management and handling of a bulk good like grain. The system and method can be used in wirelessly collecting data analytics concerning the state of the particulate goods. The nodes are distinct, untethered devices that can be freely distributed in the particulate goods so as to collect a representative sampling of conditions at different locations. Such data analytics can be applied during storage at one site, but can additionally or alternatively be applied during transportation to other sites. Portions of particulate goods may be added or removed from the system at any time, (e.g., during processing of the particulate goods, and/or during other stages of handling of the goods).

The wireless sensor nodes of the system and method can provide detailed local condition information about the stored particulate good and throughout a storage lifecycle of the particulate good. Preferably, the wireless sensor modes are designed to be substantially cheap and interchangeable after one or more stages of handling of the particulate bulk good. For example, a wireless sensor node may include a power system and operate in a way that the wireless sensor node can maintain operation during a full season of grain treatment from storage to processing which may be several months to over a year.

The system and method can additionally be integrated with a controllable system that can be used in augmenting the handling and/or processing of the particulate goods or related systems. In one variation, the system and method when used in combination with a storage container can include use of a controlled ventilation system, wherein the data analysis generated in part by the nodes can be used in augmenting control of its environmental control hardware such as the ventilation system. The system and method may alternatively be integrated with a management platform used in generating reports, triggering actions in response to state. The management platform may serve as a dashboard to a farmer, processor, end buyer, regulatory agencies, or other suitable entities. In one exemplary application, a management platform could generate alerts about the state of the particulate goods during storage. In the case of grain this could even include predicting pricing or automatically coordinating grain supply delivery.

In particular, the system and method is preferably applied to the monitoring of grain, and more specifically applied to monitoring of grain while stored in a grain bin. The system and method can alternatively be used for monitoring and managing processing of other particulate goods. The particulate goods may include other food items such as cereals, beans, nuts, spices, fruits and vegetables, cooking goods (e.g., flour), bulk food items, and/or the like. The particulate goods could alternatively be non-food items or any suitable material such as in the storage and conditioning of pharmaceutical powders, plastics, and minerals. Herein, the system and method are primarily described as it is applied to grain such as corn grain. In applying the system and method to the grain use case, storage containers are described as grain bins, and stages of processing can involve storage in a grain bin, transport between locations, and/or other processes involved in processing grain. Such descriptions and examples do not limit the system and method to use with grain, and the system and method could be similarly applied in other applications as would be well understood by someone knowledgeable in the art.

As one potential benefit, the system and method can improve quality control of grain. The system and method can monitor various properties of the grain such as biochemical makeup of the grain kernels including attributes such as protein content and oil content and the environment conditions in which the grain is stored in such as temperature, moisture, environmental gases, and the like. Such conditions can have significant impact on grain value by avoiding grain spoilage and/or by timing sales of the grain to increase profits. Similarly, by sensing the quality control of grain one can detect and mitigate risks associated with food contamination that could have a health impact in the final product. Additionally, careful and strategic environmental control and kernel biochemical detection could be used to shift the biochemical makeup and flag the system when the kernel has the optimum biochemical makeup. This is useful, but not limited, to predicting and detecting grain biochemical makeup for ethanol production where ethanol production has the most significant yield when grain has been left to mature during storage until the kernels reach optimum starch and protein content. As exemplified, such quality and environmental control can be important to farmers supplying the goods and/or processors or end buyers that use received goods.

As a related potential benefit, the system and method could provide a distributed and localized view into the grain state. The wireless sensor nodes are preferably distributed in multiple locations. Preferably, the distribution of wireless sensor nodes provides an enhanced view into the state of the grain in multiple regions. This may improve the overall analysis of the particulate good. This may additionally enable localized analysis for portions of the grain.

As another potential benefit, the system and method can be used in tracking grain during processing. Tracking of grain can be used in supply chain management. Additionally, the system and method may be used in tracking quality of sub-portions of grain collections during processing. Because, the system and method utilize distinct wireless nodes, the nodes can be mixed into the grain so that they stay mixed with the grain until an extraction process (e.g., a filtering process) separates the nodes from the grain. In this way, the system and method may not be limited to tracking at a single site but can be integrated into different processing sites such as at the farm and at a processing site. The tracking of grain could additionally be used during transportation or other stages of processing. In one exemplary implementation, the system and method may be used to track changes of quality of grain during different stages and in different modes of handling such as transport by truck, rail, barge, or ocean vessel. The records of quality could aid in the settlement discussions for payment between parties and help remedy any market claims between parties. When fully integrated at different stages, a processor or end buyer that works with multiple farms and/or suppliers can track and automatically coordinate management of their grain resources.

As another related potential benefit, the system and method may enable tracking of grain even from the point of harvest. A wireless sensor node could be first released or introduced to grain at the point of harvesting. Relating this event to a location can enable highly accurate agronomic information to be applied to the tracking of the grain. This agronomic information can be associated with the grain and/or wireless sensor node throughout processing, this could enable the farmer to market the data history of the grain to an end buyer, with the sensor being the tracking mechanism that carries the full data history through the timeline of the grain. As another potential benefit, the system and method can be resilient to individual sensor failure. The system and method preferably rely on the general collective operation of the individual node, and each individual node may be a non-critical component. In this way if a limited number of sensors fails, the system and method may continue operation. Individual sensors would not need to be replaced during a usage cycle, because the system is preferably not compromised be a limited number of failed sensors. Additionally, a compromised sensor does not need to be individually addressed, because it could be extracted at the same time and in the same manner as a functional sensor. This can address many maintenance issues of other systems.

Related to this, the usage of the nodes may be such that the nodes are considered "disposable" from the perspective of the user (e.g., the farmer). A set of nodes used in one storage cycle may not be expected to be used in the following storage cycle. This can have benefits over permanently installed or integrated solutions in that the nodes may not be subjected to repeated use in the harsh environmental conditions inside a grain bin. They may then be disposed, recycled, or reprocessed for future use.

2. System

As shown in FIG. 1, a system for monitoring storage conditions of particulate bulk goods of a preferred embodiment can include a set of wireless sensor nodes 100, an analysis engine 200, and a task manager 300. The system can additionally include a communication station 400 and/or an environmental sensing station 500. The system can additionally include controllable systems 600, which in one preferred variation includes a controlled ventilation system. The analysis engine 200 receives condition data from the nodes 100 and optionally the environmental sensing station 500 and creates particulate state analysis. The task manager 300 then acts upon the state analysis. Acting upon the state analysis may include directing the controllable system and/or changing the state of a particulate good platform.

The system may be integrated into the receptacle of storage for any particulate bulk good. In the grain use case, the system can be integrated into a grain bin but could alternatively or additionally be integrated into other environments such as a grain transport system like as a shipping container or a grain processing system.

In one variation, the system can include a single instantiation of the system where the system is installed for a single location. As a single instantiation variation, the grain may be managed within that one processing site. For a grain bin, a single instantiation would involve managing grain while being stored. For a grain transport system, a single instantiation may include monitoring conditions during transport. For a grain processing system, a single instantiation may include managing grain handling while processing. In alternative variations, multiple instances of the system as described herein can be instantiated as an integrated system as shown in FIG. 3 and FIG. 4.

The wireless sensor nodes 100 of a preferred embodiment function to be local sensing devices or beacons that can be mixed with, or otherwise positioned near, the material of interest. The wireless sensor nodes 100 (at times more concisely referred herein as nodes 100) act as wireless sensing motes or distinct devices that collect data from each of their respective locations. The nodes 100 preferably include at least one environmental sensor 110 (to monitor ambient conditions), casing 140, and a communication module 130. As the nodes preferably need environmental access, the node can include an air particulate filter integrated with the casing 140. The node may additionally include location-determining sensors 120, which may also serve as an environmental sensor 110 or be an additional sensor. As an electronic device, the nodes 100 can additionally include a microprocessor, a battery or power supply system 160, a data storage system, and/or any suitable conventionally used computational components.

Figure 5:
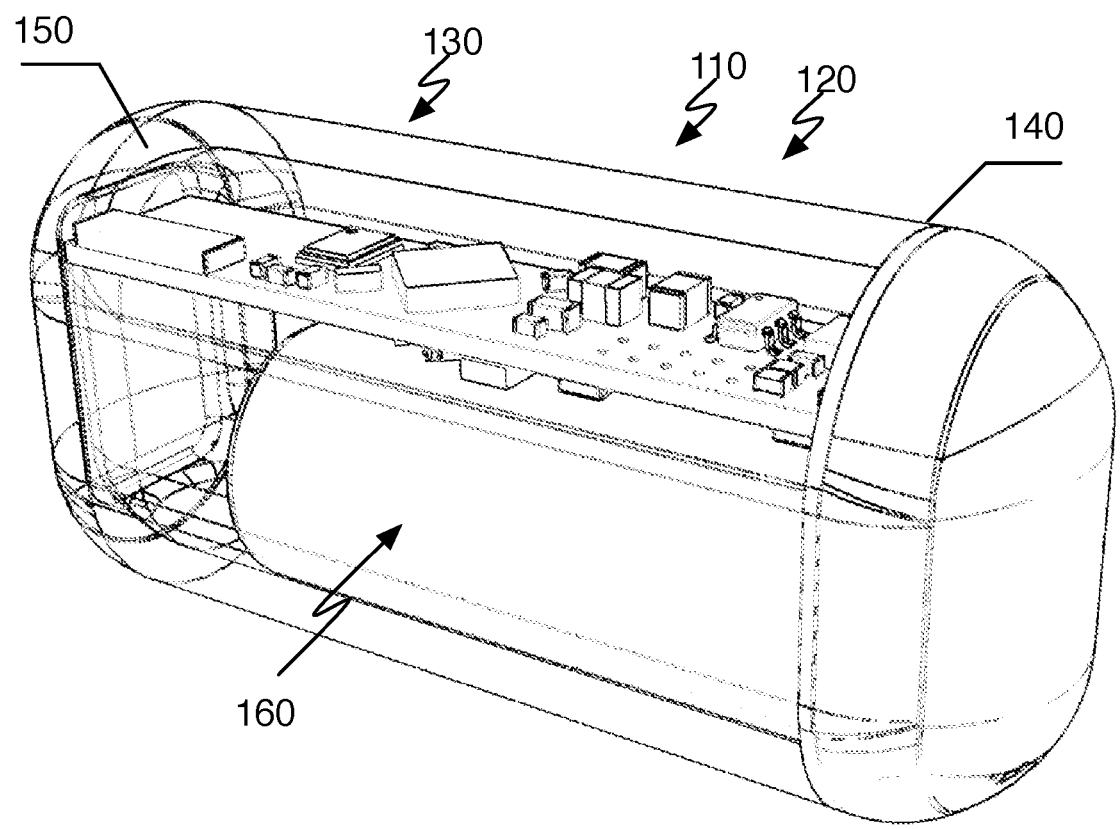
FIG. 5 is a detailed schematic representation of a node.

The nodes are preferably used such that they are dispersed within a stored quantity of particulate bulk good. The nodes should thus preferably have the appropriate size, shape, and structural features, such that the nodes can flow through and with the stored particulate bulk good. In one implementation, the casing 140 can be capsule shaped with a smooth outer surface as shown in FIG. 5. The shape of the casing 140 may alternatively be a non-smooth form and could include ridges or structures that may function to stabilize the position in the grain after being dispersed to a particular location. Any suitable shape may alternatively be used.

Another consideration in form factor of a node 100 can be that the nodes may be configured to maintain a substantially suspended position within a grain volume or, in other words, be substantially stable with any buoyancy forces. The weight, center of mass, and surface area can be arranged to address such factors. In other words, the nodes are substantially density neutral to relative to a collection of the particulate good. Herein density neutral characterizes the tendency for an item dispersed within particulate matter to flow with the matter. In other words, the buoyancy of the item is not biased such that the item would move downward or upward during matter vibration or movement. For example, dispersed nodes that are density neutral could distribute substantially randomly within a collection of grain when the agitated. The density neutral characteristic can function to prevent nodes 100 from rising to the top or sinking to the bottom of a grain bin. A node 100 that is density neutral can be sized and weighted in coordination with the density properties of the targeted particulate good (e.g., volume and weight). In one implementation, the nodes can be dispersed at various locations and different times as the good is deposited into the receptacle such that the set of nodes can sample conditions at representative locations within the volume of stored good. In another implementation with preferably density neutral nodes, the nodes can be placed into a goods receptacle at any time, and the system can be mixed/agitated for a sufficient amount of time dependent on the size and viscosity of the system.

In one variation, the form factor can make the nodes conducive for physically filtering or separating from the grain at a later stage. For example, the size may be sufficiently greater than the grain such that a sieve or mesh filter could be used to extract nodes from grain. In one variation, the node can be sized to an auger compatible size, such that it can pass through an auger during grain processing.

In another implementation, the node 100 could include a magnetically attractive portion (e.g., a metal portion or a magnet) such that a node 100 could be magnetically removed. For example, when the grain is being transported down a conveyor belt, a magnet system could collect the nodes 100. Alternatively, a filtering system could be used if the size of the node 100 and particulate good is sufficiently different.

In a preferred variation, the wireless sensor nodes 100 include Microelectromechanical (MEMS) sensors; where at least some of these sensors may be environmental 110 and location sensors 120. Alternative sensors may include any type that can carry out the intended sensor function, is durable, cost effective, and energy efficient. In this variation MEMS sensors are used because they are small, cost and energy efficient, and mass-produced. Any alternate type of sensor that meets useful goods monitoring requirements may alternatively be used.

The nodes preferably include one or more environmental sensors 110. The set of environmental sensors no included in a node may include temperature sensors, humidity sensors, volatile organic compound (VOC) sensors, barometric sensors, inertial measurement units (IMU), mass spectrometer sensors, and/or any suitable sensors. The sensors are preferably digital sensors that function to collect periodic samples of their respective metric. The temperature sensor can be a digital thermometer and used in collecting the ambient temperature. The humidity sensor can be a digital sensor that measures the ambient relative humidity. In preferred implementations the temperature and relative humidity may be used to calculate the EMC (equilibrium moisture content) of the monitored particulate good. The VOC sensor can detect and measure detect ambient VOCs, and may function to detect mold presence. The mass spectrometer sensor may be used in molecular fingerprinting the nearby environment of the node. For example, the mass spectrometer sensor may be used in oil and protein detection. The molecular makeup of the grain may change over time and during different environmental conditions that can be detected through mass spectrometry. Mass spectrometry may additionally be used to determine the moisture content within the grain. Thus, for some preferred implementations in grain storage, mass spectrometry may be used in understanding when grain is ready for different applications, such as for ethanol production, human food products, animal feed products and the like.

The nodes may preferably have location sensors 120 to determine the position, relative position, or even motion of the nodes. Possible positioning sensors include, but are not limited to: a barometer and an inertial measurement unit (IMU) sensor. A barometer can measure ambient pressure on the node 100 that may then be used to determine the relative height of the node with respect to other nodes. An inertial measurement unit (IMU) sensor may be used to measure kinematic activity experienced by the node. The IMU can include a one or more axis accelerometer and/or a one or more axis gyroscope. A one or more axis magnetometer or a basic vibrational sensor could additionally or alternatively be used. The IMU may be used in detecting motion, predicting displacement, identifying vibrations or other disturbances, and/or measuring other factors that may alter its position or orientation. As will be described below, one operating mode of the node 100 can be used to generate a location prediction within a grain bin as the node is deposited into position. In addition, a barometer and/or IMU sensor can respectively determine strength and/or effectiveness of an aeration/ventilation system and of any physical shifting of stored goods during the storage period. Used in combination, the barometer and/or IMU sensor may additionally be used to determine the approximate location of the sensor in three-dimensional space.

The nodes 100 may include a unique identifier that can be detected and communicated through wireless communication such that the data and characteristics of the nodes can be distinguished from other nodes. The identifier could additionally be used by a to limit communication to only the appropriate nodes. The identifier may also be used to identify and monitor local sections of goods. Thus, certain conditions that are only observed in a local area of the storage receptacle may be identified in the particulate state analysis, and the task manager may direct specific changes only to that localized region. An example would be a small water leak causing a subsection of particulate goods to become wet. The localized damp conditions would be potentially reported on the particulate state analysis, which may cause the task manager to direct extra "drying" ventilation towards that subsection, and/or designating and reporting that specific area for isolation or removal. The identifier may also be used to trace local sections of goods. During material agitation, transportation, separation, processing, and/or combination of receptacles containing identical types of goods, nodes may be used to uniquely identify the original source of a subsection of goods.

The operation and data collection of the various sensors of a node 100 could be synchronized where a sample is collected for each sensor at approximately the same time. Alternatively, the sensors could be controlled such that they may have different sampling timing and/or windows. In one variation, one sensor may consume more power during sensing and so that particular sensor may be used more selectively.

A casing 140 functions as an enclosure or body structure to seal the internal components of the wireless sensor node 100. The casing 140 preferably protects the components from the outside conditions. The casing 140 can preferably withstand the bulk weight of the particulate and resist environmental factors (e.g., moisture and dust) within the particulate bulk good. The casing 140 should preferably be durable for over the storage life span of the particulate. Preferably the casing 140 should be durable for 14 months, which functions to last a typical grain storage season. The casing 140 may also be suitable to last any desired duration. The casing 140 preferably includes an outer surface that may be a food grade material that comes into contact with the grain. The casing 140 additionally includes a defined internal cavity to contain electrical components of the node. The internal cavity, in one variation, may include an open-air portion. Alternatively, a portion of the defined cavity may be filled with non-conductive epoxy to further protect electrical components from environmental conditions. The cases can also be transparent to allow for external optical sensing such as in the variation where the environmental sensors 110 include a mass spectrography sensor. In addition, an internal surface of the casing 140 can be electroplated and can be used as an antenna for radio communication. In one preferred implementation, the casing 140 may be a polycarbonate mechanical casing 140. Polycarbonate has high impact strength, high modulus of elasticity, and absorbs little moisture. In addition, polycarbonate is very RF (radio-frequency) transparent (20 kHz-300 gHz). ABS (acrylonitrile-butadiene-styrene), a ceramic, and/or other suitable materials may alternatively be used for a casing 140.

The casing 140 may preferably include two metal side panels for increased rigidity to protect the battery. The metal side panels could additionally serve as a magnetically attractive element as described above.

The casing 140 may additionally include at least one defined access region that includes a filter 150 or other mechanism to promote access to sampling nearby air conditions. The filter 150 preferably enables environmental access for one or more of the sensors. For example, the humidity sensor and/or the VOC sensor may need to sample the environmental conditions outside the node. A filter 150 can be a porous sintered metal, metal mesh, plastic mesh, fibrous material, semi-permeable material, or any suitable type of filter. In some cases, hydrophobic filters may be used. The filter 150 could be a single stage filter or a compound multistage filter using different filter types. In one variation, a sintered stainless-steel filter can be used. In another variation, a metal mesh filter can be used in combination with an adhered hydrophobic fiber filter. Additionally or alternatively, a structural filter may be used, wherein a physical structure can be configured to have an intake air cavity. The intake air cavity can function to allow air access but mitigate access by particulate matter. In one implementation, the access region is the only exposed opening of the casing 140 prior to adding the filter, and thus the filter can additionally function as the cap or lid of the node.

The wireless sensor node 100 can additionally include a communication module 130 that functions to support at least outbound communication. The communication module 130 may additionally support two-way communication. In one preferred variation, the communication module may additionally support flood or mesh networking such that communication can be relayed between nodes to reach a device of the system. The communication module 130 preferably performs local wireless communication to a communication device 400 and/or an environmental sensing station 500. Alternatively, the communication module 130 of at least one node could perform cellular or satellite-based communication to communicate with a remote computing resource. Data from the node is preferably relayed to the analysis engine 200. The communication module 130 may additionally operate with fewer limitations on latency since the time scale and speed of control of agriculture storage environments usually are at the scale of hours to days. The communication module 130 preferably uses a sub-gigahertz radio frequency transmission within the FCC allocated ISM band and is preferably less than 1000 MHz such as 900 MHz. In the grain use case, corn can include a large portion of water (e.g., 10-30%), and a relatively lower frequency transmission like 900 MHz may be preferable for penetrating through the water-dense material.

The communication module 130 may accommodate low power usage. In one preferred variation, a battery may be used to power the node. Proprietary logic and sensor fusion can be used to optimize message passing and network traffic by only allowing nodes 100 in a storage environment to pass messages solely in the direction of the data collector. In one variation, the communication module 130 can additionally use a customized communication protocol that accommodates for the particular data communication. In one preferred implementation, an ultra-low power SoC (System on Chip) with an ARM based microcontroller is used.

In one variation of the system, all nodes 100 are of uniform type with identical internal components. Alternatively, multiple types of nodes may be included in the set. For example, for a preferred system of implementation where, cost, durability, and the size of the node are important factors, a specific sensor type may be too large, too expensive, or too energy inefficient to incorporate in all nodes. In addition, different sensors may vary in strength and thus how far out from the node they may be able to measure respective ambient conditions. In the situation of different sensor strengths, it may be preferable to distribute certain sensors at a greater density throughout the particulate to receive sufficient information.

The nodes 100 can include different operating modes. One operating mode can include an initialization mode, which can be used as the node is dropped into a receptacle. During an initialization mode, the node may be configured to monitor and detect a free fall as the node is deposited into the receptacle. An estimation of receptacle size may be generated from processing the kinematic data from the IMU during the free fall to determine the distance of the fall, which can be used to determine relative vertical displacements within the good. Alternatively, other location sensing processes may be performed to determine the initial position of a node. Sensor fusion or independent use of data from the air pressure sensor and/or multi-axis magnetometer can also be used to facilitate estimation of the node within the receptacle. In this mode triangulation of radio signals, relative to other nodes and external communication hubs, may also be used to estimate node location within the receptacle. In this way, the nodes may not only provide distinct particulate information from within the bin but can also be used to produce a representative map of conditions based on location.

Another operating mode can be a sensing mode, which is used during sensing and reporting (communicating to analysis engine). During a sensing mode, a node, environmental sensing station, and/or analysis engine can coordinate a sensing and/or communication schedule based on current conditions and/or battery life of the node. For example, extreme outside weather conditions may trigger more frequent sensing of particular properties (every 15 minutes), and mild weather conditions may trigger less frequent sensing (e.g., four times a day).

One mode of operation may be a battery saving mode. In this mode, the system is optimized to monitor and communicate sufficiently to maintain the particulate bulk good, while minimizing battery/energy usage. This mode functions through an ultra-low power network topology using an optimal modulation scheme: communication occurs in variable time-synchronized transmission windows, where the central analysis engine may control transmission allowances.

Other operating modes may include a transport mode used during transportation and a processing mode. Different operating modes may be initiated by the communication station or another device communicating to the node. Alternatively, some operating modes may be based on power levels, sensor data, detected kinematic events, or other properties of the node or it's environment.

The analysis engine 200 functions to transform collected data into an assessment of the particulate goods. Either directly, or over some type of communication network, the analysis engine regularly receives information from all or some nodes 100 within a storage receptacle, and its environmental sensing station 500 (if it has one). This information is analyzed and processed. Using this information, the analysis engine 200 creates a particulate state analysis. This particulate state analysis can then be sent to the task manager 300 which may then act upon receiving the state analysis. The analysis engine 200 may additionally gather external data, such as public weather reports, market prices, buyer and seller requests, and any/or all external information that may be relevant. Over time new data is gathered and the analysis engine 200 updates or creates a new state analysis for the monitored receptacle.

Once the task manager 300 has received a particulate state analysis it communicates with one or more control systems as necessary. In one preferred example, the task manager controls the ventilation system of a grain bin, which may include individually controlled vents and individually controlled fans for storage bins with multiple vents and/or multiple fans.

The task manager 300 may include a remote data analysis platform, which functions to facilitate remote access of the system over a network. As one aspect, the remote data platform can include a data management system wherein data can be stored. As another aspect, the remote data platform may present any and/or all information obtained from each observed node and environmental sensing station. This may also include global analyses made by the analysis engine over all or some observed nodes, in addition to statistical analyses, trends, historical comparisons and deviations, and predictions. The system can include web or native applications, an API, or other suitable client access interfaces that can be used for interacting with the system. The remote data platform preferably includes an account system that can be used by a system administrator to setup and monitor their system integration or integrations. In many cases, a system administrator (e.g., a farmer) will have multiple system integrations that can be managed through the remote data platform. The display may also give recommendations as to moving or selling goods. The system may preferably allow observed information to be changed and to change or override actions to be taken by the task manager. In one exemplary application, the analysis engine 200 may be used to automatically output an order recommendation, wherein the order recommendation can suggest when to sell and/or deliver the bulk good (e.g., grain) to a processing site. The recommendations may be built around targeting maximizing or at least enhancing profits, targeting particular bulk good conditions (which may be specific for different use cases), and/or other bulk good handling goals.

The communication station 400 of a preferred embodiment may act as the master device used in coordinating, directing, and/or otherwise managing the other system components. In one variation, the communication station 400 is comprised of an analysis engine 200, that functions as the processing part of the communication station 400, and the task manager 300, that directs and manages the other system components. Alternatively, the analysis engine 200 and/or task manager 300 may be managed or execute on a remote device or outside of the communication station 400. In another variation, the communication station 400 may be a communication router that functions to communicate with the nodes 100 and relay data to a remote service or platform where the analysis engine 200 and/or task manager 300 may be. The communication station 400 may be a physical device used within proximity of the nodes and/or an environmental sensing station, and thus in direct communication with the nodes. In one implementation, the communication station 400 is mounted to the outside of the grain bin. The communication station 400 preferably includes common embedded computational components to facilitate its operations, and it may be battery powered, solar/wind powered, directly powered through a connection to mains power, and/or any suitable combination.

In one preferred embodiment, the system may additionally include an environmental sensing station 500. The environmental sensing station 500 can include sensors such as a temperature sensor, humidity sensor, barometer sensor, wind sensor/anemometer, precipitation detection or measurement system, environmental gases sensor, and/or any suitable sensor, i.e., any sensor that could report useful information about the surroundings of the stored bulk good. The environmental sensing station 500 may preferably have a set of sensors that are outside of the receptacle and a second set of sensors installed inside of the receptacle, but outside of the goods to measure headspace conditions. Headspace conditions characterize the local internal environmental conditions within a storage container and above the bulk goods. In one variation, the environmental sensing station 500 includes an external environment sensing system 500 and a storage container environment sensing system. In one variation, the external environmental sensing system can be mountable outside, and the storage container environment sensing system can be an extension that functions to extend through the storage container wall for sensing access to the headspace conditions. In another variation, the environmental sensing system 500 could be mountable within the storage container and the external environmental sensing system could extend through the wall to the outside. In another variation, external environmental conditions could be collected from a remote device and/or a third-party device or service. Any alternative architecture of an environmental sensing may be used.

In one preferred implementation for grain stored in a grain bin, a weather hub may be used as an environmental sensing station 500. The weather hub measures temperature and humidity, but may measure other conditions as necessary. The environmental sensing station 500 may be integrated with and/or be part of a communication station 400, but may alternatively be a separate device in communication with the communication station 400 or other suitable component of the system.

In some variations, the system may not include an environmental sensing station 500, i.e., when no external sensor is necessary. For example, in a transportation-based instantiation of the system, an environmental sensing station 500 may not be necessary during a short transport of goods. This may occur when the goods are in transport for some short time period and external conditions are irrelevant. Additionally, a physical environmental sensing station 500 may not be used when a different device, external to the system, fulfills the role of the environmental sensing station, (e.g., internet access may be used to access local weather data from an external source, or even manual entry by a person observing external conditions may be used to instead of an environmental sensing station).

The system may include a controllable system 600, which is used to augment or alter the goods condition some way. Preferably, the controllable system of a grain bin can include a controllable aeration system. The aeration system may include a fan or multiple fans that can be activated to circulate air within the grain bin. The activation state of the aeration system and/or the aeration level may be controlled. In another variation, the aeration system can include multiple fans at different locations. The different fans may be independently controlled so as to promote targeted aeration of the grain within the grain bin. In a similar variation, the ventilation system may include a single fan but multiple controllable vents such as an array of floor vents distributed across the floor of the brain bin. The vents in addition, or as an alternative, to the fan could be controlled to alter aeration by region within the grain bin thereby allowing specific treatment of grain in select regions of the bin.

The system may additionally or alternatively include other controllable systems boo such as agitators or stirrers, other environmental control systems, and/or other mechanisms that act on the grain bin. Other control systems may be used outside of storage such as a dynamically controlling supply separators used with a conveyer belts, augers or other processing transport mechanisms. A controllable supply separator can function to direct portions of grain based on environmental conditions history experienced by that collection of grain.

In one preferred embodiment, the particulate bulk goods may be removed from the monitored storage receptacle. As shown in FIG. 4, the system may be implemented across storage, transport, processing, and/or other stages. Goods movement may be to switch storage receptacles, process the monitored goods, transport the goods, or any other alternatives. The wireless sensor nodes 100 originally dispersed in the goods may still follow along and may be used to continually monitor and track the goods. As the goods are moved and/or processed, the dispersed nodes 100 may stay connected to the same analysis engine 200, task manager 300, and/or environmental sensing station 500, or may disconnect and/or connect accordingly as desired or necessary. In one preferred example, during transfer of goods by truck from one storage facility to another storage facility, the nodes 100 stay connected to the same cloud-based analysis engine 200 the entire time. The environmental sensing station 500 that monitors them changes to one on the transport truck, and then finally to a similar environmental sensing station at the destination storage facility. The task manager 300 would similarly disconnect after leaving the original storage facility. On the transport truck the task manager may be a simpler format that only informs a display platform. At the final destination another task manager 200 would be connected and functioning with the bulk goods in their new storage facility.

In one variation, the system may comprise of multiple storage receptacles, where each receptacle may contain some particulate bulk good. The distance between receptacles may or may not be consequential. The set of nodes 100 in each receptacle is a mesh network. In one variation, multiple mesh networks may have their own distinct environmental station 600, analysis engine 200, and/or task manager 300. In this variation, a remote data analysis platform may display show information about all mesh networks. For example, a farmer may review the status of all storage bins. In another example, a processor and/or end buyer may be provided access to monitor status of grain within the processing site. In one variation, a processor or end buyer may be provided access to even review some information about grain suppliers. The remote data platform can be used for running analysis on collected data. That analysis could be for a single receptacle, a whole site (e.g., a farm or processing plant), a region, or for any suitable scope. Additionally, commands may be remotely triggered through the remote data platform. For example, a farmer may be able to remotely activate or otherwise alter the state of a controllable system by issuing a command on the remote data platform that is then communicated back to the site of the system integration. The system may include one analysis engine 200 for multiple storage receptacles, but may alternatively include multiple analysis engines 200 for each or several of the receptacles. In one preferred variation, multiple mesh networks may send information over the internet to a cloud based analysis engine. The analysis engine can then create a unique analysis for each mesh network, and/or a general analysis for multiple mesh networks. This information can then be sent to multiple task managers 300 that are distinct for each mesh network, a general task manager that controls multiple networks, or a combination of the two. The system may be customized for various possible multi-receptacle scenarios.

Figure 3A:
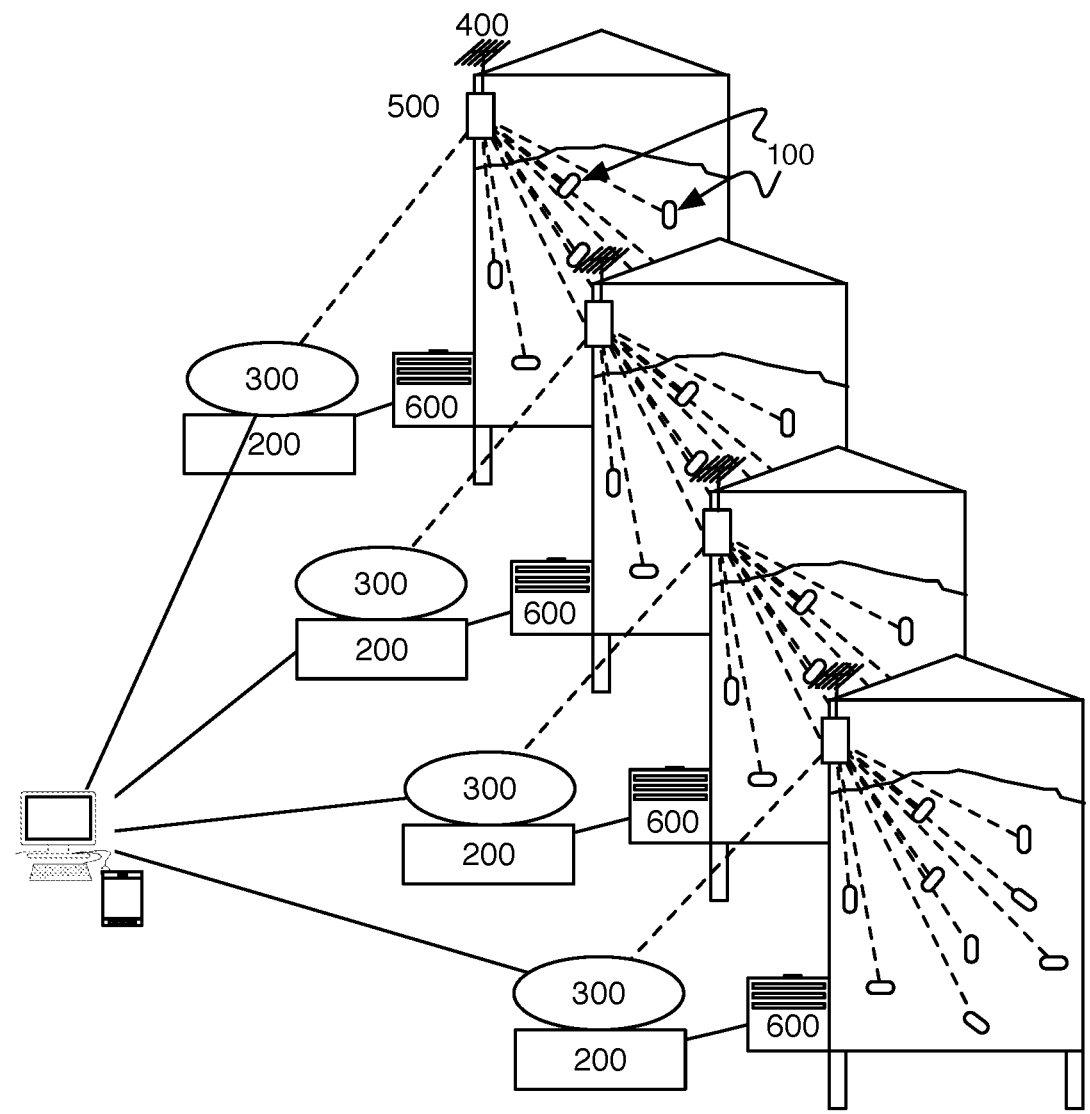
FIGS. 3A-3D are schematic representations of several variations of the system.
Figure 4:
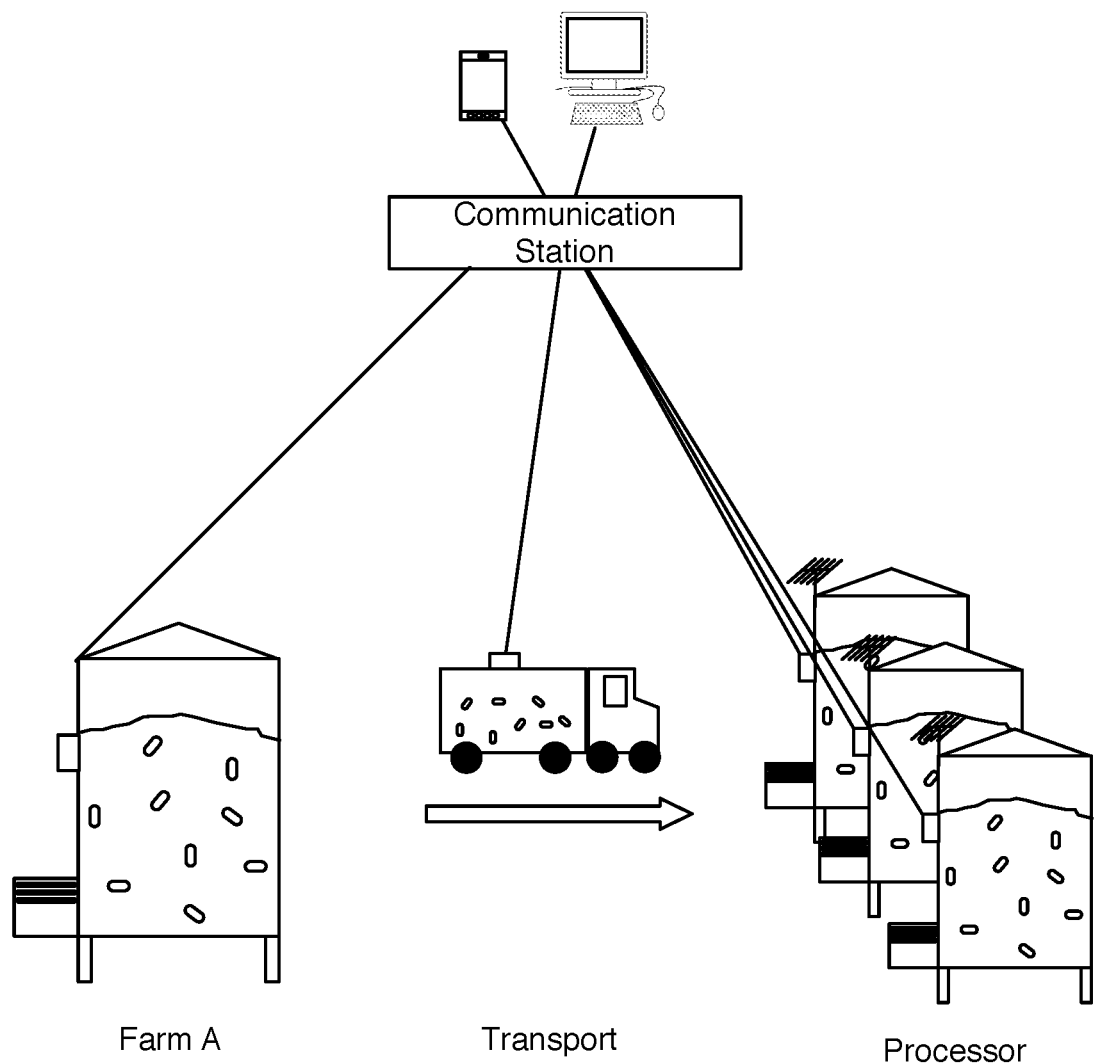
FIG. 4 is a schematic representation of the system integrated at multiple processing stages.

As shown in one exemplary multi-receptacle variation of FIG. 3A, the system may involve multiple storage receptacles, where each is monitored by its own set of nodes 100 and environmental sensing station 500. Each receptacle can have a distinct analysis engine 200 that generates a particulate state analysis for each distinct task manager 300. Each task manager 300 can operate a distinct set of controllable systems 600, but additionally sends information to a single remote data analysis platform that is shared between all storage receptacles.

Figure 3B:
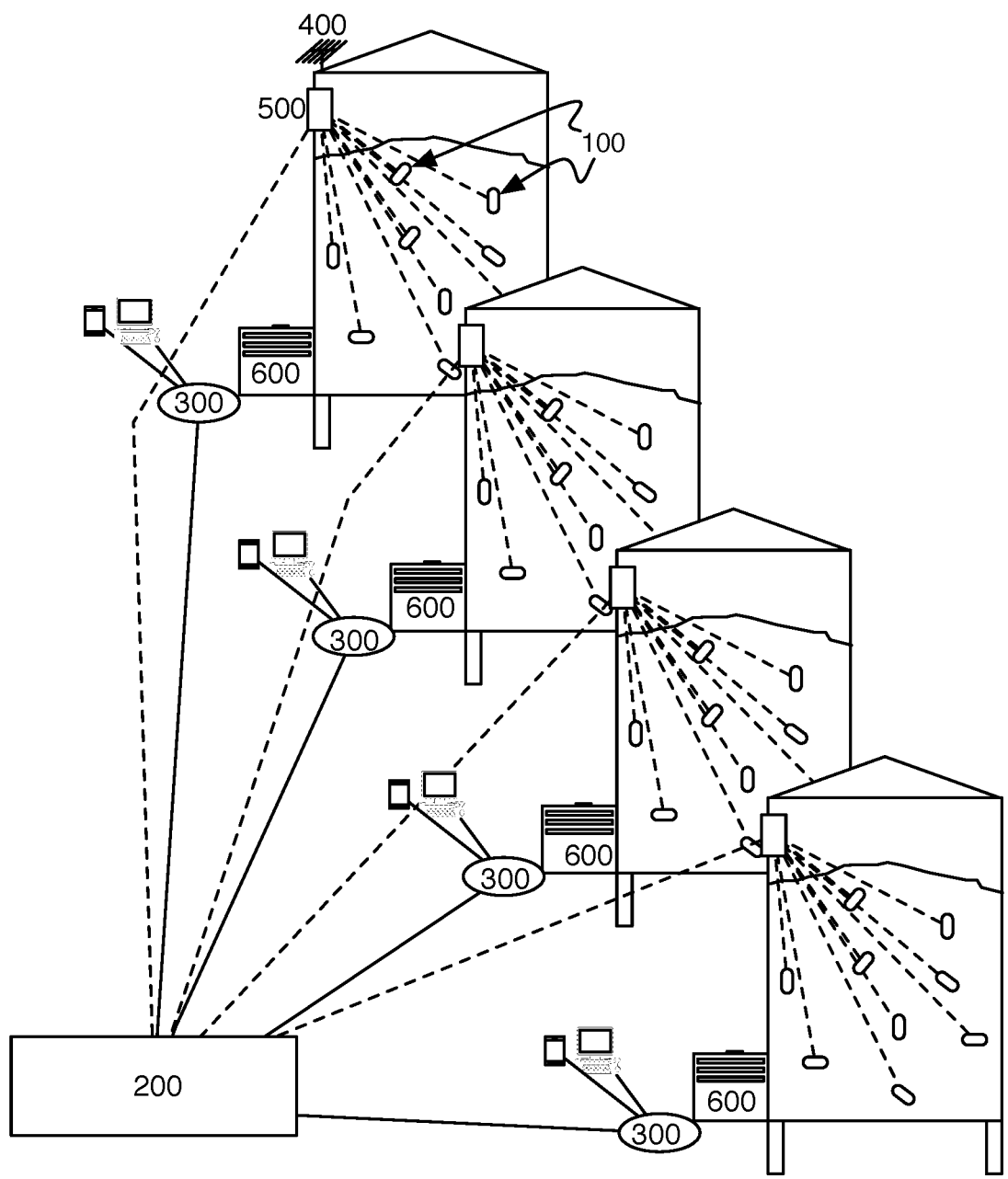

As shown in one exemplary multi-receptacle variation of FIG. 3B, multiple receptacles can alternatively share a single analysis engine 200. This may be the case when the analysis engine is located externally (e.g., on a remote server or computing platform). Collected data and information can be sent to this single analysis engine 200 that then generates a particle state analysis for each receptacle. These state analyses may be influenced by factors at other receptacles. The particle state analysis for each receptacle is then sent to the corresponding task manager 300 for that receptacle which then triggers the task manager to manage its own data analysis platform and control systems 600.

Figure 3C:
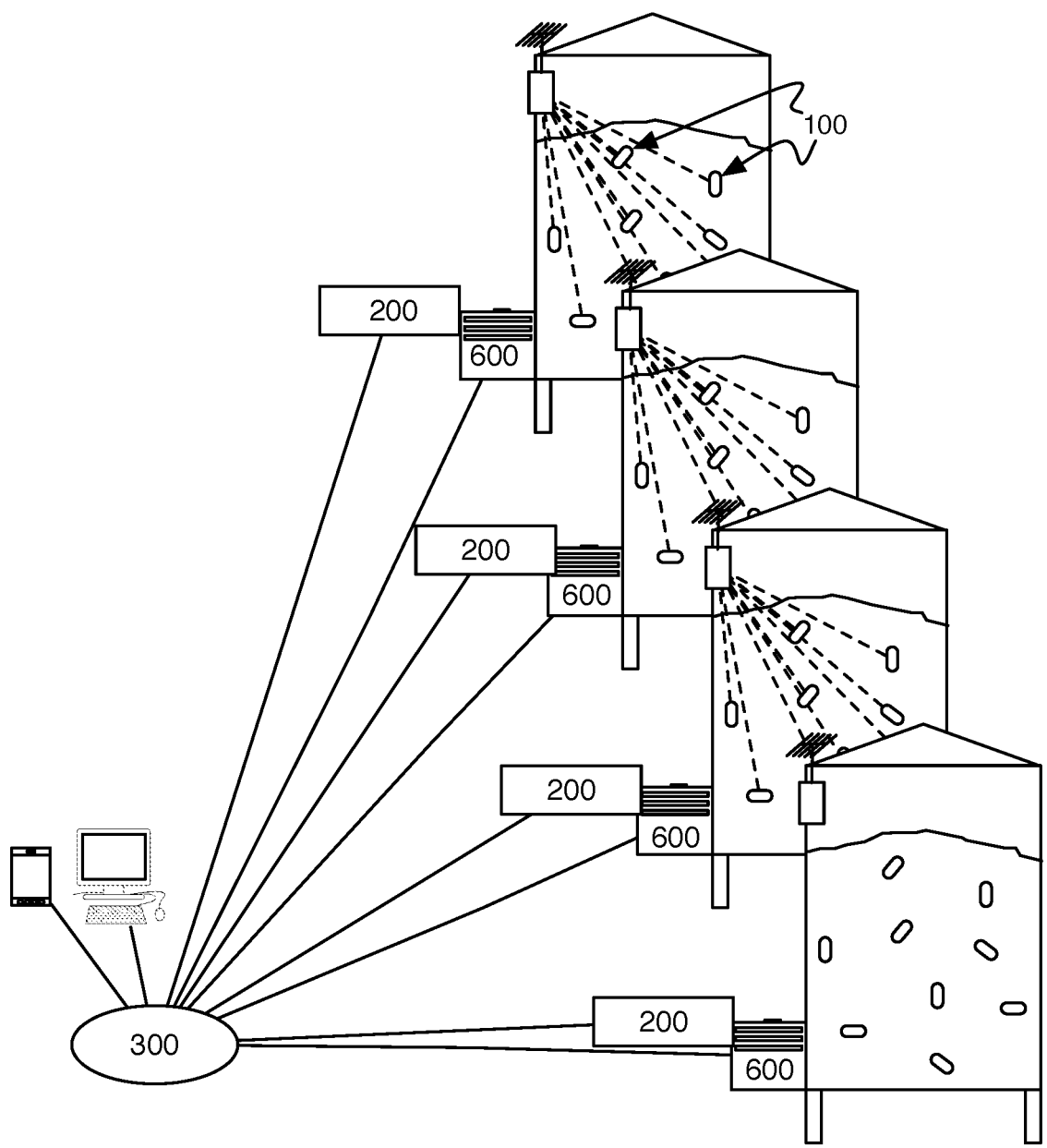
Figure 3D:
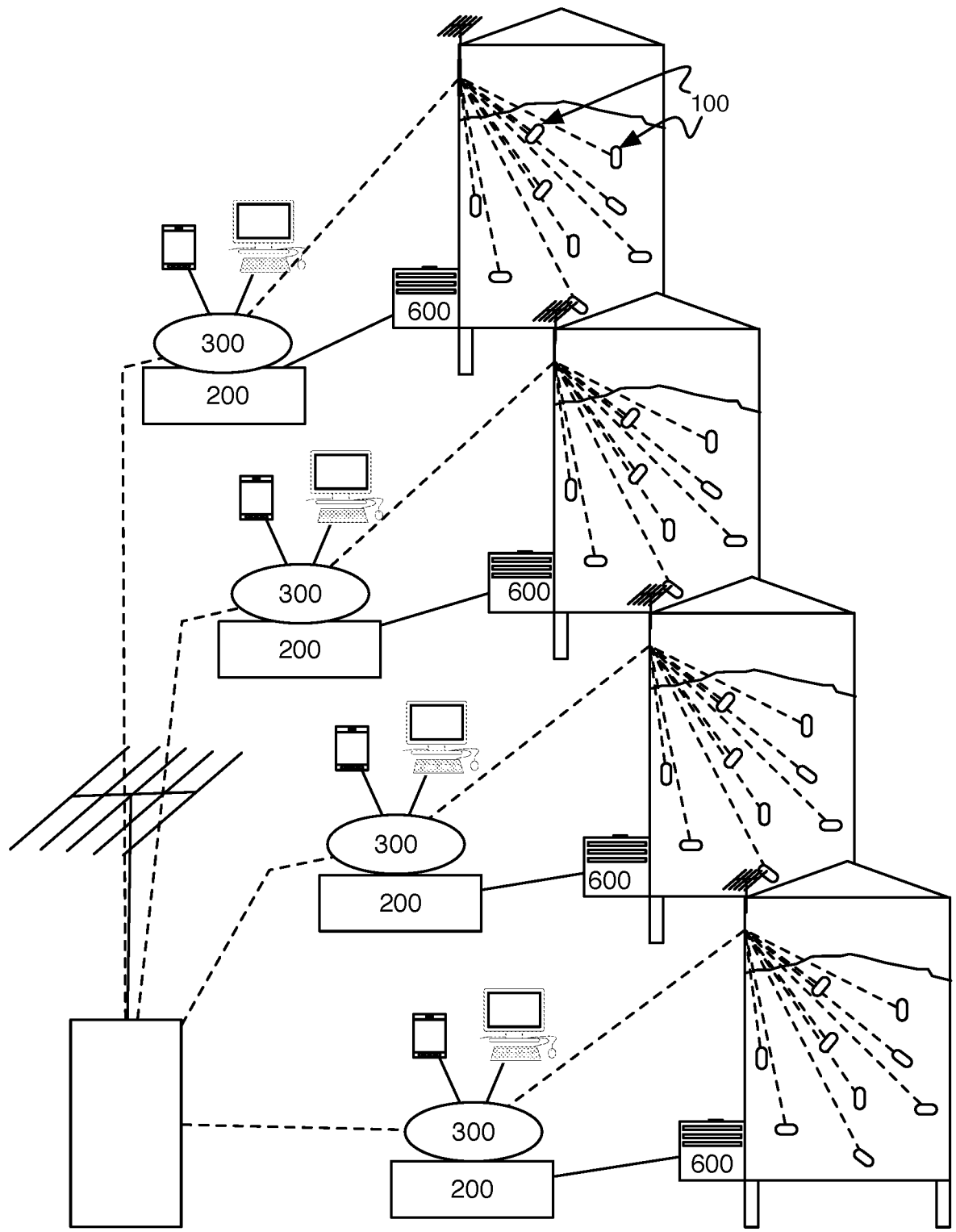

As shown in one exemplary multi-receptacle variation of FIG. 3C, each storage receptacle can have a distinct analysis engine 200. These analysis engines 200 send the state analysis generated for an individual storage receptacle to a central task manager. This central triggered task manager may then manage all controllable systems 600 from afar.

As shown in one exemplary multi-receptacle variation of 3D, all receptacles may alternatively function independent of each other, but use a shared environmental sensing station 500. Many examples of this situation exist, for example where the storage receptacles are close to each other and a single device may monitor be sufficient to monitor the weather, or in the case where an external weather service is used to monitor weather. These variations serve a non-exhaustive list of how the system may be interconnected and implemented. In addition to other possibilities not mentioned, any combination of these previously mentioned variations and/or partial combinations of these variations may also be implemented.

The system may include a single analysis engine and task manager used for a single grain bin, but there may additionally be multiple analysis engines and task managers used for a single grain bin, and as previously mentioned, there may be a single analysis engine and single task manager used across multiple grain bins. In another variation, different communication stations may be used by nodes in different stages of processing. For example, transport trucks, other storage bins, grain processing equipment may be outfitted with communication stations to track the grain at various processing stages. Data is preferably synchronized at the remote data platform. Synchronization between the various communication stations and the remote data platform may facilitate coordinated management of nodes as they are moved to different stages of processing.

Communication stations 400 and/or environmental sensing stations 500 distributed across multiple sites or systems—for storage, transportation, processing, and the like. With grain communication stations 400 may be positioned at a storage bin at a farm, possibly within a transportation device (e.g., a truck, or a conveyor belt), storage bin at a second site, at a processing site, and/or at any suitable stage. A grain communication station 400 may additionally be integrated in a harvester or other piece of equipment used during collection of the grain in the field. In this variation, the location of collection can be detected (e.g., by reading GPS location) and associated with the node 100. The nodes are preferably identifiable and the condition data and/or state analysis can be stored in association with the node identity. In this way each stage may contribute mode information and/or leverage previous information for managing that stage. In one example, a first communication station can be positioned proximal to a storage bin and configured to collect condition data of the set of wireless sensor nodes when dispersed within particulate good during storage. A second communication station can be positioned proximal to a bulk good processing site, and the second communication station can be configured to collect condition data of the set of wireless sensor nodes when detected at the processing site. The collected condition data can be synchronized a shared analysis engine 200. Alternatively, the processing site could retrieve condition data or state analysis and alter processing through a task manager 300.

3. Method

Figure 6:
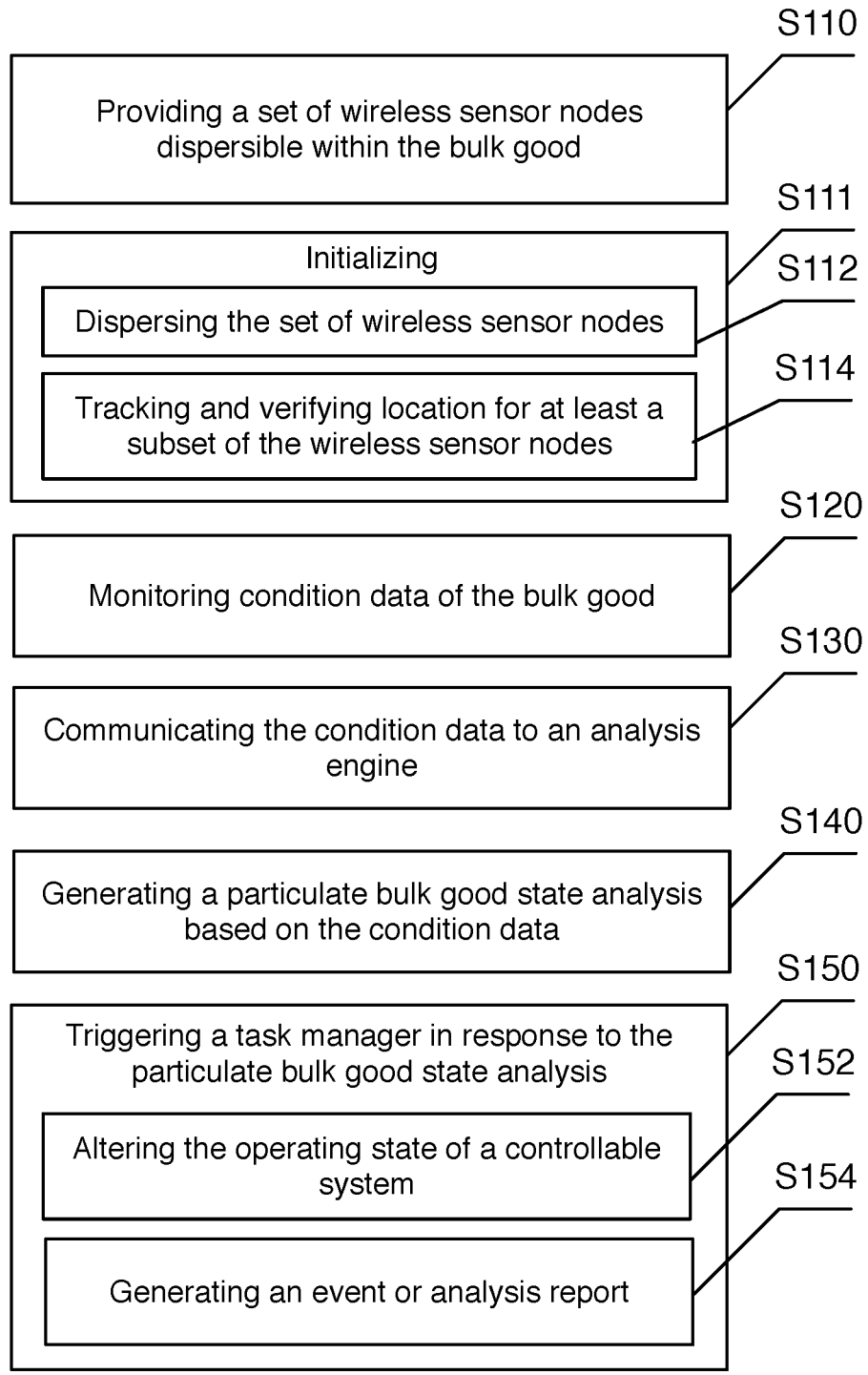
FIG. 6 is a flowchart representation of a first method.

As shown in FIG. 6, the method for managing storage conditions of particulate bulk goods of a preferred embodiment may include providing a set of wireless sensor nodes dispersible within the bulk good Silo; monitoring condition data of the bulk good S120, communicating the condition data to an analysis engine S130; generating a particulate bulk good state analysis based on the condition data S140; and triggering a task manager in response to the particulate bulk good state analysis S150. The system is preferably implemented by a system substantially similar to the one described above but may alternatively be implemented by any suitable system.

Block S110, which includes providing a set of wireless sensor nodes dispersible within the bulk good functions to provision wireless sensor nodes with the preferred properties. These nodes may preferably have environmental and location sensors, a radio frequency communication module, and a ready to use battery. In addition, the nodes provided may have preferred properties (e.g., density neutral, flowable) such that they can be dispersed in the particulate bulk good material to be monitored. The wireless sensor nodes can be substantially similar to the nodes described above.

In some preferred variations, the method may additionally include installing an environmental sensing station and/or a communication station, in or around the storage receptacle. One preferred implementation would be installing a weather hub for a grain bin. This would entail fixing the weather hub on the roof of the bin to measure external temperature and humidity and drilling a hole into the roof of the bin for the weather hub to measure the temperature and humidity above the grain within the grain bin.

In addition to or in connection to Block S110, the method may include initializing the system Sm, which may further include various processes during the setup of the system for use with a bulk good. Initiating the system may include dispersing the set of wireless sensor nodes S112 and tracking and verifying location for at least a subset of the wireless sensor nodes S114.

Block S112, which includes dispersing the set of wireless sensor nodes, functions to insert, mix, or otherwise distribute multiple wireless sensor nodes in a collection bulk good or material, such as grain. How the nodes are distributed can determine the location of data sampling within the receptacle. The required number density of nodes within the bulk may change depending on the sensor strength within the nodes. Dispersing nodes may occur as the particulate bulk good is deposited into the receptacle. In one implementation, a dispensing mechanism may automatically, or by manual intervention, disperse a node at appropriate intervals as the particulate good is deposited into the receptacle. In another implementation, dispersing the set of nodes can include mixing the particulate goods and node together until the nodes are adequately distributed. In an alternative implementation, mechanical or magnetic implements may be used in placing or moving the nodes to precise locations within the filled receptacle. Preferably, the wireless sensor nodes are distributed throughout the bulk good. More preferably, the wireless sensor nodes are evenly distributed or at least have at least one wireless sensor node present in every region. However, the method may accommodate for low density of wireless sensor nodes or for overly high density of wireless sensor nodes.

In one variation, the nodes may be dispersed with the goods during the collection of the goods. In the case of grains, dispersing a set of wireless sensor nodes can include dispersing the wireless sensor nodes incrementally while harvesting (i.e., collecting) the grain. The global position is preferably detected and associated with a wireless sensor node at approximately the time of disbursement with the grain, which functions to identify where in the field the grain was collected. This may be used to form agronomic data as the wireless sensor node monitors the grain in near proximity. Additionally or alternatively, external agronomic data collected from another source can be fed in to the system and then tracked with the grain. As the wireless sensor nodes are passed from site to site with the grain, the history and agronomic information can be traced with the wireless sensor nodes.

Block S114, which includes tracking and verifying the location for at least a subset of nodes, functions to sense the dispersed positions of a subset of the wireless sensor nodes. Verifying the location of the nodes confirms how well the nodes are dispersed such that they may accurately monitor activity throughout the entire storage receptacle. In addition, during the collection of data in block S120, nearby nodes may be alternatively shut off to preserve battery power. Verifying the sensor locations S114 includes locating the wireless sensor nodes. The locating of nodes may be accomplished by determining the dispersed position of each node or a subset of nodes. Dispersed position can include characterization of the relative position or absolute position of the nodes. The dispersed position in one variation may only provide a height estimate of the node. In another variation, the dispersed position can be an estimated relative position of the nodes in three dimensions. Determining dispersed position may be done by sensing air pressure (e.g., Measuring barometric pressure using a barometer) around each node and estimating a vertical position as part of the dispersed position. Estimating a vertical position may include determining relative height of a node with respect to other nodes using air pressure to height displacement calculations. Tracking the location of the nodes may also preferably include collecting kinematic data, detecting free fall, and generating a displacement measurement. Radio frequency triangulation, reverse 3D magnetic field localization, absolute air pressure to height displacement calculations, or other techniques may additionally or alternatively be used in identifying location of a node.

Block S120, which includes monitoring condition data of the bulk good, functions to monitor and track condition data. Monitoring condition data can generally include collecting data and analyzing the obtained data to generate a particulate state analysis.

Figure 7:
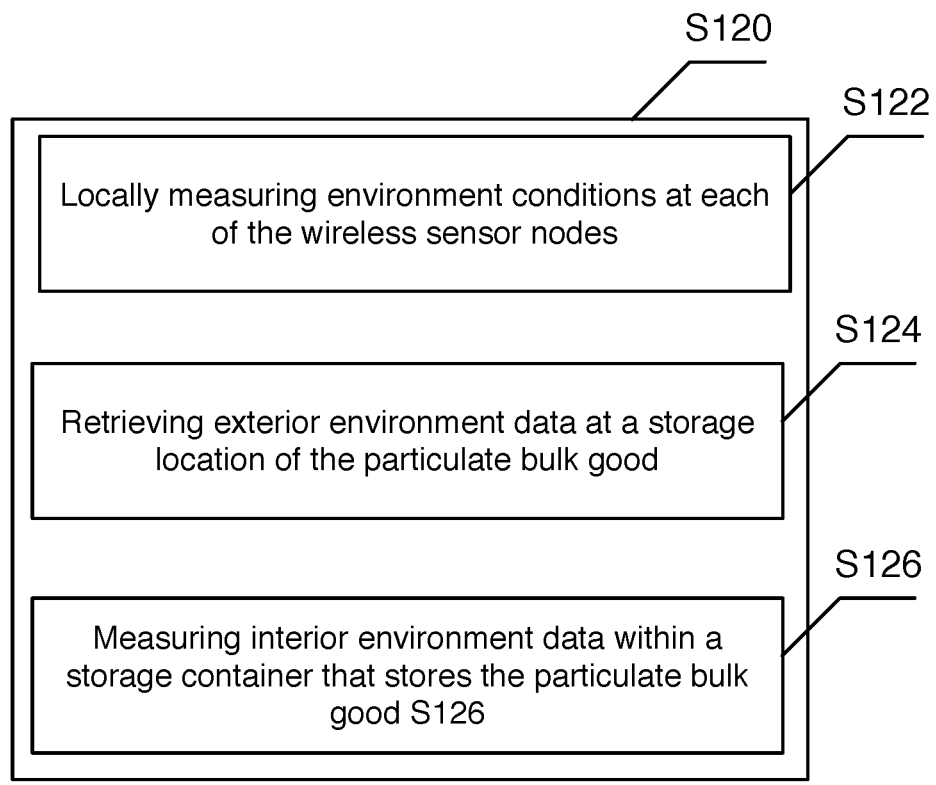
FIG. 7 is a flowchart representation of a variations of monitoring condition data.

In particular, this includes locally measuring environment conditions at each of the wireless sensor nodes S122 and may additionally include retrieving exterior environment data at a storage location of the particulate bulk good S124 and measuring interior environment data within a storage container that stores the particulate bulk good S126 as shown in FIG. 7.

Collecting data preferably functions to use the various sensors of the system in collecting data. Collecting data preferably includes locally measuring environment conditions at each of the wireless sensor nodes S122 and may additionally include retrieving exterior environment data at a storage location of the particulate bulk good S124 and measuring interior environment data within a storage container that stores the particulate bulk good S126.

Local measurement of environment conditions is preferably sensed at the nodes. Local environmental conditions at a node can capture the environment conditions in close proximity to the bulk good around each node. Locally measuring environment conditions at each of the wireless sensor nodes may include measuring temperature, measuring humidity, detecting ambient volatile organic compounds, and collecting ambient mass spectrometry data. Sensor data is preferably collected from multiple nodes at distinct locations.

The condition data could additionally include storage conditions external to the bulk goods such as storage bin headspace environmental data and exterior environment. Block S122, which includes retrieving exterior environment data at a storage location of the particulate bulk good, functions to measure or access weather or environmental data from outside of any system used to handle the bulk good. An external environmental sensing station mounted outside of a storage bin may sense the local external conditions at the site. Alternatively, data from a remote weather service could be accessed.

For a preferred implementation of grain storage, the preferred environmental sensing station is a weather hub that may collect data on weather, air temperature and humidity, headspace temperature within the grain bin, absolute humidity within the headspace and/or any other suitable metric.

Block S124, which includes measuring interior environment data within a storage container that stores the particulate bulk good, functions to sense the conditions in the headspace. A storage container environment sensing system may be used to detect the conditions. Alternatively, one or more nodes could be distributed on the top surface of the bulk good or otherwise left exposed to the headspace and used to collect condition data from the headspace. A node used in such a way may detect usage as a non-bulk good sensing node or may be configured as a non-bulk good sensing node so that collected data is treated appropriately during analysis.

In addition to collecting condition data, block S120 may include locating a dispersed position of each of the wireless sensor nodes when dispersed within the bulk good S126, which functions to collect the location data for the nodes. Collection of dispersed position data may include collecting information to determine the dispersed position of nodes with respect to each other, and may additionally include velocity and directional information of each node. Collecting this data may be similar, or even identical to, the manner described for block S114. Block S114 may provide initial position and may use account for an initial disbursement process. Block S126 can be a continuous or periodic process that may occur at regular or irregular time intervals to track the dispersed position. Node motion during storage (e.g., during grain bin agitation) and change of receptacles may also be preferably tracked during S124. With the tracking of nodes, the motion and location of subgroups of particulate bulk goods may also be tracked.

Block S130, which includes communicating the condition data to an analysis engine, functions to transfer condition data for processing. The condition data is preferably communicated at least from the nodes to an external device such as a local communication station positioned near the nodes. Alternatively, the nodes may communicate through cellular data or an alternative communication channel to synchronize condition data with a remote computing resource. The data may additionally be communicated to different locations in the case of processing being at least partially distributed between multiple resources (e.g., a communication station device and a computing platform.

Block S140, which includes generating a particulate bulk good state analysis based on the condition data, functions to analyze the obtained data and generate a state analysis of the system. Analyzing the data may include analysis of node environmental data, node dispersed position data, interior environment data within a storage container, exterior environment data, externally inputted data, and/or any type of data that can be monitored that may have an effect on the storage facility, and/or the particulate bulk stored within. Generating a particulate bulk good state analysis can be based on the combined state and/or history of the condition data. Generating a particulate bulk good state analysis can additionally be based in part on the dispersed positions of each of the wireless sensor nodes. Depending on the properties of the bin and particular factors involved in storage and storage maintenance, one, some, or all of the condition data may be used in generating a state analysis. Depending on the operating mode of the system, e.g., battery saving mode, the intervals that data is analyzed and state analyses are generated may be at regular or irregular intervals, and may even change over time. In the preferred example of a grain bin functioning on battery saving mode, state analyses may be generated once every day or week in sunny and warm weather conditions, but change to minute by minute analysis during a heavy rain storm.

In one variation, the particulate bulk good state analysis can characterize overall state of the bulk. Additionally or alternatively, the particulate bulk good state analysis can model state of sub-regions of the bulk good. Since the nodes are dispersed, the analysis engine could generate a state analysis for multiple points within the collection of goods. For example, the state analysis may characterize the state of the bulk goods as a function of height in the storage bin, as a function of grain position within the volume of the bulk good, as a function of proximity to a node, or in any suitable manner. Localized state analysis can be continuous or by regional classifications.

In addition to generating a state analysis from internal components of the system, the analysis engine may also access external information with regards to the stored particulate good (e.g., market prices for grain, and buyer/seller requests). With the additional information the generated state analysis may include suggestive information, such as buying or selling, or relocating.

In some preferred variations, bulk goods may be moved from one storage receptacle to another receptacle, either for storage for some other purpose, e.g., processing, or transport. The method, rate, and output of the state analysis generated may change during this process as necessitated. In a preferred example, grain is moved from a storage bin to a transport truck. State analysis for the bin may include long term care analysis on maintaining proper grain moisture with distinct orders for the operation of ventilation control systems. As mentioned above, this type of storage may be battery optimized such that analyses are generated at irregular intervals as necessitated by weather information. In contrast, during grain transport state analyses may be generated frequently to take into account extreme transport conditions. This data may not include weather hub information, since there is a good likelihood a transport truck wouldn't have a weather hub, and may likely have only minimal orders for controlled systems, such as for warning signals.

Block S150, which includes triggering a task manager in response to the particulate bulk good state analysis functions to use and act on the state analysis. A task manager can be configured application instructions to direct any suitable process, system, or device.

In one variation, triggering a task manager S150 can include altering the operating state of a controllable system S152. As described above, various controllable systems may be used. One preferred controllable system can be a ventilation system of a grain bin used to store the grain. Altering the operating state can include changing the operating state of the ventilation system. Changing the operating state may include opening or closing grain bin roof hatches. In another variation, altering the operating state can include altering operations for a dynamic aeration system, that can include activating or deactivating, setting the aeration magnitude, triggering different locations of aeration (in a multi-location venting or multi-fan option), and/or altering the aeration system in any suitable manner. In one variation, the aeration may be dynamically controlled according to a spatial analysis of the grain such that the ventilation system can be controlled to apply different ventilation in different subregions of a storage bin.

Figure 8:
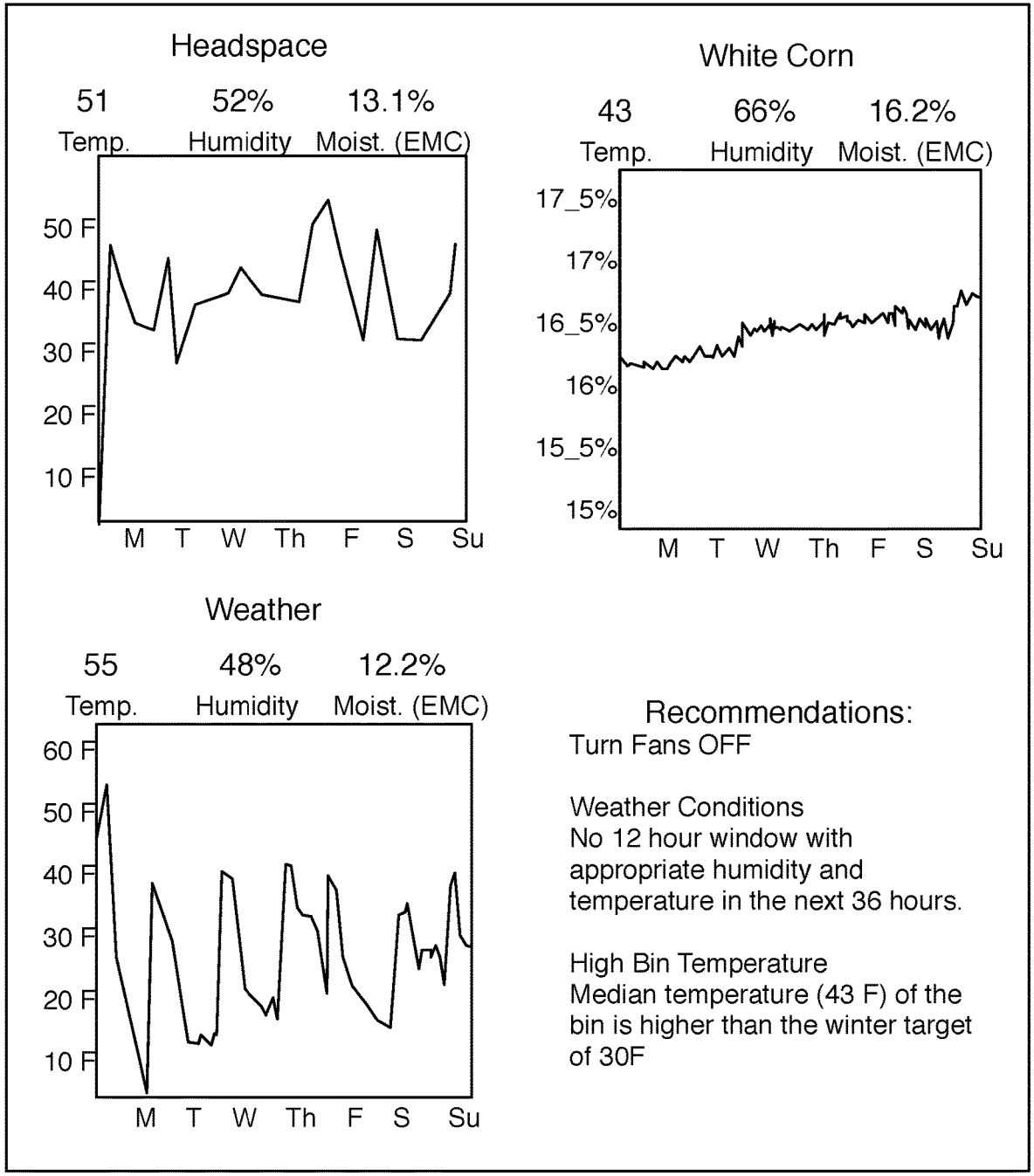
FIG. 8 is a schematic representation of an exemplary analytics dashboard.

In another variation, triggering a task manager S150 can include generating an event within a remote data platform and/or presenting an analysis report S154. Generating an event can function to send a notification or alert. The notification or alert could be an update on the current conditions, an alert as to the processing state of the bulk good. For example, a farmer may get an alert if an unexpected change in the conditions occurs. As another example, a farmer may get an alert based on a prediction for grain readiness. In presenting a report, various aspects of grain state analysis can be presented in an interactive dashboard or a static summary. Presenting the report may occur, or be made available to or accessed on the remote data platform. In some cases, alerts can additionally be generated by the report. The report could be a static report, or an interactive report made available through an administrator interface such as in the example shown in FIG. 8. The alerts could be transmitted in any suitable format. In other cases, the report may be a comprehensive analysis of everything that was measured and determined about the good condition. In some preferred examples, the report may also include the opportunity for some external person, or device, to input new information and/or new commands to alter directly how some controlled systems operate, or alter how the task manager operates the controlled systems.

In some preferred variations, collecting condition data may occur at multiple receptacles. Collected condition data from each receptacle may be sent to a distinct location for each receptacle, analyzed there, and have a distinct task manager to direct control systems for the receptacle. Alternatively, multiple receptacles may be analyzed distinctly, with a single task manager, such as in the case of a centralized output display for multiple storage receptacles. Another alternative would be multiple receptacles analyzed by a central analysis engine, e.g., one located in the cloud, with a distinct actor for each receptacle. For all these possibilities each receptacle may have no environmental sensing station, a distinct environmental sensing station, or share an environmental sensing station between multiple receptacles. Alternatives with any combination mentioned, or any partial combination may also be used.

When used in a multi-site variation, the method may be used within a processing facility to alter handling of the bulk goods based on the state analysis of the grain. In some implementations, where the processing facility is receiving bulk goods from multiple storage bins (e.g., from one or more farm), the handling of bulk goods could dynamically change based on the monitored conditions like to a node detected at the processing site. This change may be applied even though the conditions and state analysis are based, at least in part, on the state of bulk code at another location.

In a variation where a processing site must lookup and access stored state analysis, each node can be identifiable. A node may be uniquely identifiable. Alternatively, each node may be identified through a storage bin identifier, a farm identifier, or any suitable scope of identifier. During the collection of data and generation of a state analysis, the associated data can be stored in a record associated with the identifier. That record may be stored in a remote computing platform as part of a bulk good conditions and/or analysis database. In this way, the method may involve identifying a wireless sensor node at the processing site, retrieving the particulate bulk good analysis associated with the identifier, and augmenting processing of the bulk good based in part on the retrieved particulate bulk good state analysis. For example, when sorting grain or transporting along a conveyor, the processing site may direct the grain for different storage bins for different uses (e.g., food-grade use, animal feed use, etc.) A communication station could be positioned along the conveyor, detect and identify a node in the grain, access the state analysis, and then trigger a task manager system to alter the routing of a section of grain in proximity to that detected node.

In some preferred variations with multiple storage receptacles. Stored material in these receptacles may be split or combined any type of fashion. Collecting data during and after transfer may be used to track subsections of the particulate bulk good, such that a subsection may be traced to its original source, and/or the unique properties of the subsection can be individually monitored and possibly acted upon. For example, grain supplies from two different farms may be mixed in a grain bin from a supplier. The mixture ratio and the conditions of that collection of grain can be better understood because the nodes from two farms were mixed together.

In connection with the nodes being identifiable, the condition data and/or state analysis could be updated throughout the lifecycle by collecting additional condition data, identifying the node(s), and updating the appropriate record. Subsequent or updated state analysis could additionally be performed and stored in association with the record. In this way the condition of the grain can be tracked and analyzed in a connected manner as it is stored, transported to another site, subsequently stored at another site, and/or processed in any suitable manner.

As one aspect, the method can include managing power and/or communication of the set of nodes. The nodes are expected to last a full cycle, and managing power and communication can be used to satisfy this target while enhancing data quality. The sensing sample rate and/or the communication frequency may be dynamically altered based on power. Additionally, power-conserving modes may cycle various subsets of the nodes through a sleep mode to conserve power. A particular example may be when nodes are close enough to each other such that environmental sensors from multiple nodes overlap in the obtained information. Power may be managed by alternating nodes in sleep mode and data collection mode to optimize power conservation without sacrificing information gain. Furthermore, message transmission windows can be shortened to preserve power or number of transmissions windows per hour can be decreased to further save power.

The systems and methods of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A system for managing a particulate bulk good comprising:
    a set of wireless sensor nodes, wherein each wireless sensor node comprises a set of environmental sensors configured to collect condition data of the particulate bulk good proximal to the wireless sensor node, wherein each wireless sensor node comprises configuration to convey at least partial position information of the wireless sensor node when dispersed within the particulate bulk good, and;
    an analysis engine that is configured to generate a particulate state analysis from the condition data wherein the particulate state analysis is at least partially based on position information; and
    a task manager that is configured to act on the particulate state analysis.

2. The system of claim 1, wherein the set of environmental sensors comprises at least one of a temperature sensor, a humidity sensor, a volatile organic compound sensor, and a mass spectrometer sensor.

3. The system of claim 1, wherein the wireless sensor node comprises a barometer and wherein the configuration to convey at least a partial dispersed position is configuration to estimate an elevation metric from a barometric measurement from each wireless sensor node.

4. The system of claim 1, further comprising an environmental sensing station that comprises an external environment sensing system and a storage container environment sensing system.

5. The system of claim 1, further comprising a controllable system coupled to a storage bin for the particulate bulk good; and wherein the task manager is configured to control the controllable system.

6. The system of claim 5, wherein the controllable system is a controllable aeration system coupled to the storage bin.

7. The system of claim 1, further comprising a remote data analysis platform, and wherein the events triggered in the data analysis platform are controlled in part by the task manager.

8. The system of claim 1, further comprising at least a first communication station positioned proximal to a storage bin configured to collect condition data of the set of wireless sensor nodes when dispersed within particulate good during storage and a second communication station positioned proximal to a bulk good processing site, the second communication station configured to collect condition data of the set of wireless sensor nodes when detected at the processing site.

9. The system of claim 1, wherein the wireless sensor nodes are substantially density neutral in comparison with the particulate bulk good.

10. The system of claim 1, wherein the particulate bulk good is grain; and wherein each of the wireless sensor nodes further comprises a communication module that is configured to communicate in a frequency range less than 1000 MHz.

11. A method for managing a particulate bulk good comprising:
providing a set of wireless sensor nodes dispersible within the bulk good;
monitoring condition data of the bulk good, which comprises of at least locally measuring environment conditions at each of the wireless sensor nodes, wherein each of the wireless sensor nodes are identifiable;
storing a record of local ambient conditions for each of the wireless sensor nodes;
communicating the condition data to an analysis engine;
at the analysis engine, generating a particulate bulk good state analysis based on the condition data;
triggering a task manager in response to the particulate bulk good state analysis; and
at a processing site, identifying a wireless sensor node, retrieving particulate bulk good analysis associated with an identifier of the wireless sensor node, and augmenting processing of the grain based in part to the retrieved particulate bulk good state analysis.

12. The method of claim 11, further comprising at least partially locating a dispersed position of each of the wireless sensor nodes when dispersed within the bulk good; and wherein generating a particulate bulk good state analysis is further based on the dispersed positions of each of the wireless sensor nodes.

13. The method of claim 12, wherein locating the dispersed position of each of the wireless sensor nodes comprises each of the wireless sensor nodes sensing barometric pressure, and estimating a vertical position as part of the dispersed position.

14. The method of claim 11, wherein monitoring condition data of the bulk good further comprises retrieving exterior environment data at a storage location of the particulate bulk good and measuring interior environment data within a storage container that stores the particulate bulk good.

15. The method of claim 14, wherein locally measuring environment conditions at each of the wireless sensor nodes comprises measuring temperature, measuring humidity, detecting ambient volatile organic compounds, and collecting ambient mass spectrometry data.

16. The method of claim 11, wherein triggering a task manager in response to the particulate bulk good state analysis comprises generating an event within a remote data platform.

17. The method of claim 11, wherein triggering a task manager in response to the particulate bulk good state analysis includes altering the operating state of a controllable system.

18. The method of claim 17, wherein altering the operating state of a controllable system comprises changing operating state of a ventilation state of a storage bin used to store the particulate bulk good.

19. A system for managing a particulate bulk good comprising:
a set of wireless sensor nodes, wherein each wireless sensor node comprises a set of environmental sensors configured to collect condition data of the particulate bulk good proximal to the wireless sensor node;
an analysis engine that is configured to generate a particulate state analysis from the condition data;
a task manager that is configured to act on the particulate state analysis; and
at least a first communication station positioned proximal to a storage bin configured to collect condition data of the set of wireless sensor nodes when dispersed within particulate good during storage and a second communication station positioned proximal to a bulk good processing site, the second communication station configured to collect condition data of the set of wireless sensor nodes when detected at the processing site.

* * * * *